United States Patent [19]

Herrmann et al.

[11] Patent Number: 5,155,247
[45] Date of Patent: Oct. 13, 1992

[54] USE OF ORGANORHENIUM COMPOUNDS FOR THE OXIDATION OF MULTIPLE C—C-BONDS, OXIDATION PROCESSES BASED THERON AND NOVEL ORGANORHENIUM COMPOUNDS

[75] Inventors: Wolfgang A. Herrmann, Giggenhausen; Dieter M. Fritz-Meyer-Weg, Munich; Werner Wagner, Munich; Josef G. Kuchler, Munich; Georg Weichselbaumer, Hoenwart; Richard Fischer, Grosskarolinenfeld, all of Fed. Rep. of Germany

[73] Assignee: Hoechst Aktiengesellschaft, Frankfurt am Main, Fed. Rep. of Germany

[21] Appl. No.: 470,086

[22] Filed: Jan. 25, 1990

[30] Foreign Application Priority Data

Jan. 27, 1989 [DE] Fed. Rep. of Germany ....... 3902357

[51] Int. Cl.⁵ .............................................. C07F 13/00
[52] U.S. Cl. ........................................ 556/46; 502/167
[58] Field of Search ........................................... 556/46

[56] References Cited

U.S. PATENT DOCUMENTS 3,316,279 4/1967 Fenton ............................. 260/348.5
3,518,285 6/1970 Fenton et al. ................... 260/348.5
4,090,978 5/1978 Welsh et al. ......................... 502/159

FOREIGN PATENT DOCUMENTS 89122437 6/1989 European Pat. Off. .

OTHER PUBLICATIONS

S. Pummel and D. Schnurpfeil, *Technetium compounds as Catalysts in Hydroperoxide Decomposition and Epoxidation Processes, Oxidation Communication*, vol. 6, Nos. 1–4 pp. 319-329.
Schmidt, M. and Schmidbauer, H.; *Trimethylsilylperrhenat Chem. Ber.* 92 (1959) pp. 2667-2669.
Schmidbaur, M. and Koth, D; Chem. Zeitung 100 (1976) pp. 290-291.
Herrmann, Wolfgang; Methylrhenium Oxides: *Synthesis from R₂O₇ and Catalytic Activity in Olefin Methanesis*, Angewandle Chemie. 100 (1988) pp. 420-422.
Milas, N. A. and Sussman, S., "The Hydroxylation of Unsaturated Substances", The Journal of the American Society, vol. 59, 1937, pp. 2345-2347.
Milas, N. A., and Sussman, S., "The Hydroxylation of the Double Bond" The Journal of the American Society vol. 58, 1936, pp. 1302-1304.

*Primary Examiner*—Patrick P. Garvin
*Assistant Examiner*—E. D. Irzinski
*Attorney, Agent, or Firm*—Connolly and Hutz

[57] ABSTRACT

Compounds of the formula $$(R^{11}Re)_k O_l R^{12}{}_m \cdot L_n \qquad (III)$$

in which $R^{11}$ is a hydrocarbon group which is bonded to the rhenium via a carbon atom to which at least one hydrogen atom is still attached, $R^{12}$ is aliphatic hydrocarbon radical which may contain silicon bridge atoms, or is an unsubstituted or substituted phenyl radical, L is a ligand which is bonded to the rhenium metal via one to three oxygen and/or nitrogen atoms, and the index k is 1 or 2, the index l is an integer from 1 to three times k, the index m is zero or an integer from 1 to twice k, and the index n is an integer from 1 to three times k, and in which the indices k, l, m and n are selected such that their combination satisfies the 5-, 6- or 7-valence of rhenium.

The invention also provides compounds of the formula $$(polymer)_f (CH_3ReO_3)_g \qquad (VI)$$

in which the rhenium compound $CH_3ReO_3$ is bonded to the polymer via amine or amide nitrogen in the polymer. It further provides for the use of compounds of the formula $R^1{}_a Re_b O_c$ (I) in which a is 1 to 6, b is 1 to 4 and c is 1 to 14 and the total of a, b and c is such that the 5-valence to 7-valence of rhenium is satisfied, with the proviso that c is not greater than three times b, and in which $R^1$ represents an optionally fluorinated hydrocarbon, or of compounds of the formula $(R^{11}Re)_k O_l R^{12}{}_m \cdot L_n$ (III) or $(polymer)_f (CH_3ReO_3)_g$ (VI), as catalysts for the oxidation of multiple C—C bonds and also provides processes of this type.

8 Claims, No Drawings

USE OF ORGANORHENIUM COMPOUNDS FOR THE OXIDATION OF MULTIPLE C—C-BONDS, OXIDATION PROCESSES BASED THEREON AND NOVEL ORGANORHENIUM COMPOUNDS

DESCRIPTION

The use of organorhenium compounds for the oxidation of multiple C—C-bonds, oxidation processes based thereon and novel organorhenium compounds The invention relates to the use of certain organorhenium compounds for the oxidation of multiple C—C bonds, oxidation processes based thereon, in particular for the preparation of epoxides and optionally diols by oxidation of olefinic compounds and for the preparation of diketones or $\alpha,\beta$-olefinically unsaturated monoketones by oxidation of alkynes, in each case with hydrogen peroxide using organorhenium compounds, and to novel organorhenium compounds.

It is known that metal oxides act selectively as oxidizing agents for unsaturated organic compounds of different categories. For instance, the binary oxides $M_xO_6$ of the metals (M) vanadium ($V_2O_5$), molybdenum ($MoO_3$) and osmium ($OsO_4$) in particular are used in practice, for example as catalysts for converting olefins into epoxides. In these reactions, 1,2-diol derivatives can also be produced, and in the case of $OsO_4$, the cis-glycols can be produced stereospecifically. These metal oxides are often not used as stoichiometric reagents but in the presence of hydrogen peroxide, tert-butyl hydroperoxide, m-chloroperbenzoic acid and so on in only catalytic amounts. Although the reaction mechanisms are not known in detail, the action of catalyst systems of this type (for example metal oxide/$H_2O_2$) is ascribed to hydroperoxo-metal completes as the actually effective catalyst species (structural unit M—O—OH).

The catalyst system $OsO_4/H_2O_2$ has particular importance for the selective oxidation of olefins to form cis-1,2-diols. In this case, catalytic amounts of osmium tetroxide are sufficient. A particularly well known reagent is Milas' reagent: $H_2O_2$/tert-butanol/$OsO_4$ (N. A. Milas and S. Sussaman, J. Am. Chem. Soc. 58 (1936) 1,302–04 and N. A. Milas and S. Sussaman J. Am. Chem. Soc. 59 (1937) 2,345–47).

However, in this connection, the abovementioned metal oxides also have disadvantages, in particular high cost (osmium), high toxicity (osmium), lack of selectivity for the formation of epoxides and cis-1,2-diols from the olefinic precursors (chromium, molybdenum, tungsten) and the short life of the catalyst under the given reaction conditions (in particular, $OsO_4/H_2O_2$/tert-butanol).

The object is therefore to provide a simple-to-handle, storable, non-toxic and effective catalyst system which ideally is easily accessible and which achieves the desired selectivity in the oxidation of olefins and certain alkynes. 1,2-Diols and epoxides are of great interest for further industrial processing and so are 1,2-diketones and $\alpha,\beta$-olefinically unsaturated monoketones.

The obvious idea of using, instead of the oxidation catalysts known from the literature, oxides of the element rhenium which is adjacent to osmium and molybdenum in the periodic table and which is many times cheaper than osmium, these oxides having the formula $Re_xO_y$, has not been verifiable in practice. For instance, the oxides $Re_2O_7$, $ReO_3$ and $Re_2O_5$, in the presence or absence of other oxidizing agents such as hydrogen peroxide and tert-butyl hydroperoxide, are either inactive or unselective in the oxidation of olefins. Only two very similar reports appear in the literature concerning the use of rhenium compounds, in particular rhenium oxides, rhenium halides and perrhenates, as catalysts for oxidation with oxygen at $-50°$ to $+125°$ C. (U.S. Pat. No. 3,316,279) and with hydrogen peroxide at $100°-150°$ C. (U.S. Pat. No. 3,518,285). In both cases, mixtures of epoxides and ketones were obtained. The oxidation with oxygen according to U.S. Pat. No. 3,316,279 can also employ "oxidation modifiers", namely organic nitrogenous compounds, in particular organic cyanides, pyridines and quinolines which are intended to halt the reaction to a certain extent at the epoxide stage and to suppress rearrangements; if they are left out, consequent reactions occur such as the formation of condensation products (by dimerization of the epoxides to form substituted dioxanes or polymerization to form polyethers) and the formation of $\alpha$-hydroxycarbonyl compounds by further oxidation of the epoxides. Moreover, the process according to U.S. Pat. No. 3,316,279 is intended to be carried out at pressures from 1 to about 250 atmospheres, i.e. operation at elevated pressure is virtually obligatory, as can also be seen from the examples. However, reactions under elevated pressure require increased expenditure on plant.

Applicant's own attempts to use the abovementioned rhenium oxides, for example $Re_2O_7$ and $ReO_3$, as catalysts for olefin oxidation were likewise unsuccessful. Similarly, $Na[ReO_4]$, $NH_4[ReO_4]$ and $[N(n-C_4H_9)_4][ReO_4]$ proved ineffective, as did organometallic mixed compounds such as the monomeric derivative (trimethylstannoxy)rheniumtrioxide of the formula $[(CH_3)_3SnO]ReO_3$ described by W. A. Herrmann et al.(W. A. Hermann, J. G. Kuchler, J. K. Felixberger, E. Herdtweck and W. Wagner, Angew. Chem. 100 (1988) 420–422) and the compounds $[(CH_3)_3SiO]ReO_3$ (M. Schmidt and H. Schmidbaur, Chem. Ber. 92 (1959) 2,667–2,669) and $[(C_6H_5)_3SiO]ReO_3$ (H. Schmidbaur and D. Koth, Chem. Zeitung 100 (1976) 290–291).

It is known from the paper by W. A. Herrmann et al., loc. cit., that of the true organometallic compounds of rhenium, methylrhenium trioxide $CH_3ReO_3$ in the presence of $AlCl_3$ and tetramethyltin brings about the metathesis of open-chain olefins and also the catalytic ring-opening polymerization of cycloolefins to form polyalkenamers. The same paper discloses that methylrhenium oxide is methylated by treatment with dimethylzinc to form a sublimable, lemon-yellow methylrhenium oxide of the formula $(CH_3)_4Re_2O_4$, i.e. a compound containing 6-valent rhenium. This compound too, in the presence of tetramethyltin and aluminum chloride, catalyzes the metathetic ring-opening polymerization of cyclopentene.

Finally, the above paper discloses that $(CH_3)_4Re_2O_4$ is converted by further methylation with dimethylzinc to $(CH_3)_6Re_2O_3$, i.e. likewise to a compound containing 6-valent rhenium. According to said paper, this compound is capable of catalyzing the ring-opening polymerization of cyclopentene even in the presence only of $AlCl_3$, i.e. without the presence of the cocatalyst $Sn(CH_3)_4$ which is necessary in other cases.

It was certainly not possible to conclude from this and the other references that organorhenium compounds also act as catalysts for the completely different reaction of the oxidation of multiple C—C bonds, particularly in the absence of a cocatalyst.

Surprisingly, it has now been found that certain organic compounds of rhenium are suitable as highly active catalysts for the oxidation of multiple C—C bonds, in particular for the selective conversion of olefins into 1,2-diols or epoxides, if the said compounds are used with hydrogen peroxide in a liquid medium.

The present invention accordingly provides for the use of compounds of the general formula $R^1{}_a Re_b O_c$ (I) in which a is 1 to 6, b is 1 to 4 and c is 1 to 14 and the total of a, b and c is such that the 5-valence to 7-valence of rhenium is satisfied, with the proviso that c is not greater than three times b, and in which the $R^1$ moieties are identical or different and represent a non-aromatic hydrocarbon radical having 1 to 10 carbon atoms or aralkyl having 7 to 9 carbon atoms and $R^1$ may be at least partially fluorinated, and the compounds do not contain more than three groups having more than 6 carbon atoms per rhenium atom and the carbon atom in the α-position still has attached to it at least one hydrogen atom, and for the use of novel compounds of the formula $(R^{11}Re)_k O_l R^{12}{}_m \cdot L_n$ (III) in which $R^{11}$, $R^{12}$, L, k, l, m and n have the meaning given below, and also for the use of novel compounds of the formula $(polymer)_f \cdot (CH_3 ReO_3)_g$ (VI), in which the rhenium compound $CH_3 ReO_3$ is bonded via amine nitrogen or amide nitrogen to the polymer and in which the quotient g/f expresses the ratio by weight of the two components and is in the range between 0.01 and 0.2, preferably between 0.02 and 0.1, as catalysts for the oxidation of multiple C—C bonds.

The invention also provides compounds of the formula $(R^{11}Re)_k O_l R^{12}{}_m \cdot L_n$ (III) in which $R^{11}$ is a non-aromatic hydrocarbon radical having 1 to 10 carbon atoms or aralkyl having 7–9 carbon atoms which in each case is bonded to the rhenium via a carbon atom to which at least one hydrogen atom is still attached, and advantageously these are alkyl radicals having 1 to 9 carbon atoms and cycloalkyl having 5 to 10 carbon atoms, $R^{12}$ is a linear or branched aliphatic hydrocarbon radical having 1 to 10 carbon atoms, which may also contain up to 3 silicon bridge atoms, or a phenyl radical which is unsubstituted or contains up to 3 substituents from the group comprising alkyl and/or alkoxy jointly having at most 6 carbon atoms or contains up to five fluorine atoms, L is a ligand which is bonded via one to three oxygen atoms and/or nitrogen atoms to rhenium and the index k is 1 or 2, the index l is an integer from 1 to three times k, the index m is zero or an integer from 1 to twice k and the index n is an integer from 1 to three times k.

The indices k, l, m and n must be selected such that their combination satisfies the 5-, 6- or 7-valence of rhenium; the ligand L may be 1-, 2- or 3-dentate and may itself be neutral or anionic.

In the formulae I and III, $R^1$ and $R^{11}$ are a non-aromatic hydrocarbon radical having 1 to 10 carbon atoms or aralkyl having 7 to 9 carbon atoms, such as benzyl, which in each case is bonded to the rhenium via a carbon atom to which at least one hydrogen atom is still attached, in particular alkyl radicals having 1 to 10 carbon atoms or cycloalkyl having 5 to 10 carbon atoms. Suitable alkyl radicals are methyl, ethyl, propyl, isopropyl and the various butyl, pentyl, hexyl or octyl radicals, such as ethylhexyl, and decyl radicals; other suitable radicals are cycloalkyl radicals such as cyclopentyl, cyclohexyl, alkylated cyclohexyl such as hydrogenated toluyl, xylyl, ethylphenyl, cumyl or cymyl, and 1-norbornyl. Particular preference is given to methyl.

The terms alkyl and cycloalkyl naturally imply that the groups contain no multiple bonds. $R^1$ may be at least partially fluorinated. However, for steric reasons it is inadvisable to have more than three groups of more than six carbon atoms per rhenium atom in compounds I and III; advantageously, the compounds contain only at most one group of this type.

The invention also provides the abovementioned compounds of the formula $(polymer)_f \cdot (CH_3 ReO_3)_g$ (VI).

The invention also provides a process for the preparation of epoxides by oxidation of olefinic compounds with hydrogen peroxide in the presence of catalysts, and a further, optional reaction to form diols, which comprises oxidizing olefins of the formula $YCZ=CZ-(CX_2)_n R^2$ (II) in which $R^2$, X, Y, Z and n have the meanings given below at a temperature of −30° to +80° C., preferably of 0° to 40° C., in a liquid medium in the presence of rhenium compounds of the abovementioned formula $R^1{}_a Re_b O_c$ (I) in which $R^1$, a, b and c have the meanings given above, or in the presence of compounds of the formula $(Re^{11}Re)_k O_l R^{12}{}_m \cdot L_n$ (III) as claimed in claim 1 or in the presence of compounds of the formula $(polymer)_f \cdot (CH_3 ReO_3)_g$ (VI), as previously defined, and a) isolating the epoxides obtained or
b) converting the epoxides obtained in the presence of the same catalysts into 1,2-diols or
c) converting the epoxides obtained in the customary manner with bases into 1,2-trans-diols or
d) converting the epoxides obtained in the customary manner with acids into cis-trans mixtures of 1,2-diols.

In the formula II, n represents 0 or an integer from 1 to 28; X is H or F; Y is H, alkyl or a mono-olefinically unsaturated or poly-olefinically unsaturated, unbranched or branched, open-chain or cyclic hydrocarbon radical having 2 to 28 carbon atoms, for example alkyl having 1 to 10 carbon atoms or aryl having 6 to 10 carbon atoms, or $COOR^3$. Z represents H or an aromatic or non-aromatic hydrocarbon radical having 1 to 6 carbon atoms, which may be cyclic, for example cyclohexyl, but is preferably an open-chain alkyl having 1 to 4 carbon atoms. The two symbols Z may also simultaneously represent CO groups which are bonded in the o-position to a benzene radical, as in naphthoquinone, or may form a cycloaliphatic ring together with C=C as in cyclohexene, 1-methyl-1-cyclohexene, cycloheptene, cyclooctene, cyclooctadiene, cyclooctatetraene, cyclododecene, cyclohexadecadiene or limonene. The substituents Z may be identical or different. $R^2$ is H, halogen, an acyclic hydrocarbon radical without triple bonds having up to 24 carbon atoms, which may contain up to 5 double bonds, as in squalene, aryl having up to 10 carbon atoms and which may contain 1 to 3 substituents on the ring which are insensitive to the oxidation conditions used, ω-oxoalkenyl, $COOR^3$ or $OR^4$, where $R^3$ is alkyl or aryl and $R^4$ is alkyl, aryl or trialkylsilyl $R^5{}_3 Si$. The alkyl groups in $R^5$ contain 1 to 5, preferably 1 to 3, carbon atoms. In $R^3$ and $R^4$, alkyl in each case represents those with 1 to 15, preferably 1 to 6, carbon atoms and aryl represents phenyl which may contain a further one to three substituents on the ring which are inert under the oxidation conditions used, such as halogen, for example fluorine, chlorine or bromine, $NO_2$, $OR^6$ and/or alkyl. The radicals $R^6$ are identical or different and may be hydrogen or alkyl having 1 to 4 carbon atoms. $(CX_2)_n$ and $R^2$ jointly have at most 28 carbon atoms. Y, $(CX_2)_n$ and $R^2$ may also form a cycloaliphatic ring system together with the group $CZ=CZ$ which may contain up to 5, preferably up to 3 olefinic bonds or up to two carbonyl groups. Ring systems of this type are present for example in pinene and dipentene (limonene).

Halogen $R^2$ may be fluorine, chlorine, bromine or iodine. If Z is hydrogen and $R^2$ is halogen, the latter is preferably bromine. Compounds in which at least one $X=F$ are for example 4-(perfluoro-n-hexyl)-1-butene of the formula $(n-C_6F_{13})-CH_2-CH_2-CH=CH_2$ and perfluoropropene $C_3F_6$. The number of chain units n varies preferably in the range from 1 to 12 and in particular up to 8.

The invention also provides a process for the oxidation of the formula $R^7C=C=CR^8$ (IV) and of alkynes of the formula $R^9C=CR^{10}$ (V) in which $R^7$ to $R^{10}$ are in each case alkyl having 1 to 4 carbon atoms or aryl containing 1 or 2 aryl nuclei such as naphthyl, biphenyl or in particular phenyl and the aryl may in each case be identical or different and may have other substituents which for their part are insensitive under the oxidation conditions used. This process converts cumulenes into hydroxy compounds whose hydroxyl group is located at the carbon atom with the least number of hydrogen atoms, and alkynes into 1,2-diketones or, if at least one of the radicals $R^9$ and $R^{10}$ is bonded to the acetylenic group by a CH-group, into $\alpha,\beta$-olefinically unsaturated monoketones. These oxiations are likewise carried out using rhenium compounds of the formulae I, III and VI as defined above with hydrogen peroxide at a temperature of $-30°$ to $+80°$ C., preferably of $0°$–$40°$ C., in a liquid medium.

According to another embodiment of the invention, it is also possible to oxidize compounds of the formula $R^{13}HC=CHR^{14}$ (VII) in which $R^{13}$ represents aryl with up to 10 carbon atoms and $R^{14}$ represents H, $CH_3$ or aryl having up to 10 carbon atoms and in which the aryl radicals are identical or different with hydrogen peroxide at a temperature of $-30°$ to $+80°$ C., preferably of $0°$–$40°$ C., in a liquid medium in the presence of rhenium compounds of the formulae I, III or VI as defined above. This arrangement produces predominantly aldehydes. Suitable starting materials for this embodiment of the invention are for example styrene, the various vinyltoluenes and stilbene. Here, too, the aryl may have other substituents which are insensitive under the oxidation conditions used, as for example in 2,3,4,5,6-pentafluorostyrene.

The compounds of the formula I are partly known (W. A. Herrmann et al. Angew. Chem. 100 (1988) 420–422) and partly the subject of earlier European Patent Application P 89 122 437.0; however, their suitability as oxidation catalysts is novel and was not foreseeable. On the contrary, they are the first organometallic compounds of rhenium which it is possible to use successfully for carrying out oxidation processes. By virtue of their solubility properties, they are particularly suitable as homogeneous catalysts. They also have the particular advantage that they can readily be synthesized from commercially available $Re_2O_7$ with the aid of commercially available substances which bring about the transfer of organic groups, for example in the case of $R^1=CH_3$ by reaction with commercially available tetramethyltin or commercially available dimethylzinc. Said compounds are insensitive to air and moisture, water and acid, have a long shelf life at room temperature and are highly active catalysts in combination with hydrogen peroxide, inorganic peroxides such as alkali metal peroxides, in particular sodium peroxide, and also percarboxylic acids and their salts such as m-chloroperbenzoic acid, peracetic acid and magnesium monoperoxophthalate, for oxidations according to the invention.

The compounds of the formula III differ from those of the formula $R^1_a Re_bO_c$ (I) essentially in that they additionally contain nitrogenous bases and/or oxide oxygen or oxo oxygen or hydroxyl which are complexed with the rhenium. In the radical $R^{12}$, alkyl can be, for example, methyl, ethyl, propyl, or one of the butyl, pentyl, hexyl, octyl or decyl radicals. Examples of substituted phenyl radicals are the tolyl, xylyl and anisyl radicals.

The ligand is, for example, an amine such as ammonia, a primary amine $H_2NR$, a secondary amine $HNR_2$ or a tertiary amine $NR_3$, in which R can be a branched or unbranched alkyl having 1–18 carbon atoms, an aliphatic azacycle such as quinuclidine, an aromatic azacycle such as pyridine and its ring-substituted and fused derivatives such as 8-hydroxyquinoline, a O,I'-, N,O- or N,N'-chelate ligand such as 2,2'-bipyridine, 2-aminopyridine, 2-(aminomethyl)pyridine, a substituted piperazine, an aminosubstituted piperidine or pyrrolidine, a methoxy-substituted pyridine such as 2-methoxypyridine, a 1,3-diketone such as acetylacetone, a 1,2-diketone such as diacetyl or pentane-2,3-dione, a $\beta$-aminoalcohol such as 2-aminoethanol, 2-aminophenol, 2-amino-1-butanol and ephedrine, a $\beta$-aminoaldehyde, a $\beta$-aminoketone, a 1,2-diimide, a $\beta$-aminoether such as 2-(aminomethyl)tetrahydrofuran, an aromatic N-oxide such as 2,2'-bipyridine-N,N-dioxide and pyridine-N-oxide, a 1,2-diamine such as ethylenediamine or a hydroxycarboxylic acid such as tartaric acid and its esters.

The ligand L coordinated to the rhenium atom may also be bonded to other metals by coordinate bonds, for example in $CH_3ReO_3\cdot[(NH_2C_6H_5)Cr(CO)_3]$, $CH_3ReO_3\cdot[(NC_4H_4)Mn(CO)_3[$ and $CH_3ReO_3\cdot$[aminoferrocene].

The compounds of the formula III can be obtained simply by reacting the precursor $R^{11}ReO_3$, for example $CH_3ReO_3$, in an organic solvent, for example methylene chloride, diethyl ether, tetrahydrofuran or toluene, with the corresponding ligands L at room temperature and then evaporating the solution to dryness under reduced pressure or isolating the adduct by crystallization. If desired, the product can be purified by distillation, by recrystallization or by sublimation under reduced pressure. As a rule, the resulting substances are stable to air, heat and water.

Suitable liquid media for carrying out the oxidation reactions are organic solvents, for example tetrahydrofuran, monhydric alcohols having 1 to 5 carbon atoms such as methanol, ethanol, the various propanols and butanols, and aromatic hydrocarbons such as toluene and the various xylenes. Another suitable liquid medium is a two-phase system of water on the one hand and water-immiscible organic solvents on the other hand, in which the hydrogen peroxide is dissolved. A solution of hydrogen peroxide in tert-butanol is particularly suitable.

In the simplest form of the invention for operation and use, the procedure is as follows:

a) A catalyst solution is prepared which contains about 10–30 mg of $CH_3ReO_3$. If tert-butanol is used for preparing this solution, the solution is a deep yellow color and has a shelf life of several weeks at −30° C., for example in a freezer chest, without diminution of the activity. This is a particular advantage of the catalysts according to the invention. The solution therefore does not need to be freshly prepared for each batch. It is possible to increase the batch sizes many times over without incurring any disadvantages.

b) The solution prepared in a) is added with stirring to the hydrocarbon to be oxidized, which is optionally dissolved in a non-oxidizable organic solvent, in such a way that the highly exothermic oxidation reaction does not cause the mixture to boil. There are then various possibilities for carrying out the reaction. It is advantageous to work in the temperature range from 0° C. (ice cooling) to 50° C. However, it is also possible to work at lower temperatures. If relatively low temperatures are employed, for example −30° to +10° C., although the reaction runs more and more slowly with progressively lower temperatures, the oxidation of the olefins leads more and more selectively to the epoxide, and further reaction to form the diol is suppressed at progressively lower temperatures. If the intention from the start is to form 1,2-diols, it is recommended to work at temperatures above 10° C. in the given range. The formation of 1,2-diols is favored in that the oxidation is highly exothermic, and the higher the starting temperature the more the reaction medium is heated and consequently the faster the reaction proceeds.

Both in the oxidation of the olefins and of the cumulenes and alkynes, the reaction medium advantageously contains 1 to 30% by weight of $H_2O_2$. If special safety precautions are taken, it is also possible to use solutions in which the proportion of $H_2O_2$ is higher. Advantageously, the solution should not contain any water, although the presence of water is not harmful, since water is formed in the stoichiometric amount from the hydrogen peroxide during the reaction.

c) If an excess of peroxide is present, this can be destroyed catalytically by adding $MnO_2$. The batch is then worked up by customary methods, for example by distillation. The catalyst $CH_3ReO_3$ can be recovered (proved using a combination of gas chromatography, mass spectrometry and infrared spectroscopy).

The catalysts used according to the invention have a high efficiency. Generally, the catalyst is present in the reaction medium in an amount from 0.01 to 7% by weight, preferably from 0.03 to 1.0% by weight. However, in particular cases, it is also possible to use it in greater or lesser concentrations. There is virtually no consumption of the catalyst during the reaction, as befits the use of the term catalyst. It is easily possible to oxidize for example a ten thousand fold molar amount of olefin with the catalyst before regeneration is necessary. The rate of oxidation naturally also depends on the reaction temperature.

If olefins of the formula II are oxidized with the aid of the catalyst proposed according to the invention, then in the temperature range from −30° to +40° C. these olefins are initially converted selectively into the corresponding epoxides, as has been shown from a kinetic study using cyclohexene and also trans-4-octene as examples. The greater the temperature constancy, the better the selectivity in many cases. The degree of conversion is also influenced very favorably by maintaining the temperature constant. The optimal conditions in individual cases are often governed also by the structure of the alkene or alkyne which is to be oxidized. It is possible for the initially formed epoxides to be converted in a subsequent reaction into the corresponding 1,2-diols. In the case of the $OsO_4$-catalyzed olefin oxidations according to Milas et al., loc. cit., except with allylalcohols, the 1,2-diols and subsequent oxidation products such as ketols are always produced, but not epoxides.

In a further embodiment of the invention, the catalyst $CH_3ReO_3$ can also be used in the form in which it is taken up (immobilized) on a polymer which contains amine or amide nitrogen. Generally in this case, a compound (polymer)$_f \cdot (CH_3ReO_3)_g$ (VI) is formed in which the rhenium compound is bonded via amine nitrogen or amide nitrogen and in which the quotient $g/f$ gives the ratio by weight of the two components and is in the range of between 0.01 and 0.2, preferably between 0.02 and 0.1. The polymers which are to be used therefore have nitrogen-containing groups at their surface, and the nitrogen atom may be present not only in aromatic groups but also in aliphatic groups and moreover in amide groups (an example is poly(4-vinylpyridine) which is marketed under the name Reillex—cf. Aldrich Catalog No. 22,696-3). In this embodiment, the polymer substance need not serve as a substrate only but can, if suitable substituents are selected, also act as a reaction-controlling component (promotor). The degree of coating of the substrate can moreover be used to control the reaction rate, the conversion and the selectivity of the oxidation. The great advantage of the compounds VI is furthermore that the catalyst can readily be separated off again after the reaction has ended, for example by simple filtration, and regenerated, and the activity and also the conversion and selectivity are only slightly reduced, if at all, in subsequent reaction batches.

In an advantageous embodiment, it is also possible to proceed by using a dissolved catalyst of the formula I in which $R^1$ is $CH_3$ and, having used this catalyst, removing it from the solution by reacting it with a polymer which contains amine or amide nitrogen and obtaining the catalyst either as a compound of the formula VI or regenerating it from this form by treatment in high vacuum at a temperature of at least 200° C. as a compound of the formula I in which $R^1$ is $CH_3$.

In the characterizations of individual substances in the following examples, the abbreviations have the following meanings: s singlet, d doublet, t triplet, q quartet, sept septet, m multiplet, br broad signal shape, sst very strong, st strong and EI-MS electron impact mass spectrum.

The starting materials for the following examples were prepared as follows:

(A) Preparation of methylrhenium trioxide $CH_3ReO_3$

The synthesis of $CH_3ReO_3$ from $Re_2O_7$ and $Sn(CH_3)_4$ is only successful if it is carried out with the rigorous exclusion of moisture. For this reason, well dried solvents are required. Advantageously, the reaction vessel (for example Schlenk tube) is kept for some time before use at 400°-600° C. under high vacuum and the $Re_2O_7$ is subsequently weighed in.

10.00 g (20.64 mmol) of dirhenium heptoxide $Re_2O_7$ (76.8% by weight of Re) were dissolved in 90 ml of anhydrous tetrahydrofuran. Meanwhile, the solvent was rapidly added with vigorous stirring, for example using a magnetic stirrer, in order to avoid agglomeration of $Re_2O_7$. To the solution obtained in this way, which can have a slightly brownish color, 3.15 ml (22.71 mmol; 1.1-fold excess) of commercially available tetramethylstannane Sn(CH$_3$)$_4$were added. Since this reagent is toxic, all operations must be carried out with suitable safety precautions, for example under powerful fume extraction. The reaction mixture was then boiled under reflux for 4 hours. Longer reaction times had no adverse effect on the reaction. After cooling the solution to room temperature, the solvent was slowly removed under oil pump vacuum until the residue had a paste-like consistency. Significant amounts of CH$_3$ReO$_3$ can then sublimate off. For this reason, further removal of the solvent was only carried out after the apparatus had been provided with a cold finger condenser cooled to between −10° C. and 0° C. (circulating cryostat).

After the solvent had been completely removed, the product was isolated in the form of colorless needles at about 80° C. in the said vacuum by sublimation onto the cooled sublimation finger condenser. The yield of analytically pure substance was 4.85 g (94% of theory, according to the reaction equation Re$_2$O$_7$ + Sn(CH$_3$)$_4$ → CH$_3$ReO$_3$ + [(CH$_3$)$_3$SnO]ReO$_3$).

The gray residue was taken up in 40 ml of tetrahydrofuran. The solution was filtered through a layer of Al$_2$O$_3$ approximately 2 cm in depth. From the colorless filtrate, by removal of the solvent, it was possible to isolate the compound [(CH$_3$)$_3$SnO]ReO$_3$ as an analytically pure colorless powder; the yield was 8.12 g (95% of theory based on the equation given above).

Data for methylrhenium trioxide

Melting point 106° C.—IR (cm$^{-1}$, KBr): 1,002 sst, 950 sst, br[ν(Re=O)]. —$^1$H-NMR (CDCl$_3$, 28° C.): δ(CH$_3$)=2.61 s. —$^{13}$C-NMR (CDCl$_3$, 28° C.): δ(CH$_3$)=19.03 [$^1$J(C,H)=138 Hz]. —$^{17}$O-NMR (CDCl$_3$, 28° C.): δ(O) =829 ppm. —EI-MS: m/z=248/250 (molecule-ion, with the appropriate isotopes present $^{185}$Re/$^{187}$Re). The substance can be kept at room temperature without decomposition.

CH$_3$ReO$_3$: calc.: C 4.82, H 1.20, O 19.26, Re 74.72; (249.21): found: C 4.84, H 1.19, O 19.30, Re 74.78.

(B) Preparation of the catalyst solution 25 ml of 30% strength H$_2$O$_2$ (of analytical quality) were added to 100 ml of tert-butanol and stirred for one hour with 30 g of anhydrous MgSO$_4$. The magnesium sulfate was then filtered off. The oxidation solution obtained was carefully kept under an atmosphere of nitrogen. To 2.68 ml of this solution, 20 mg of solid methylrhenium trioxide were added. The solution, consisting of the catalyst CH$_3$ReO$_3$ (30 mmol/liter) and the oxidizing agent H$_2$O$_2$ became instantly yellow. The solution can be kept at 0° C. for a relatively long time and retains its activity at this temperature and at even lower temperatures. The amount of catalyst can be reduced to 3 mmol/liter, but then, for the same conversion, the oxidation reaction takes longer.

EXAMPLES

Examples 1–35

Oxidation of alkenes, cumulenes and alkynes

The relevant alkene or alkyne (cf. Table 1) was added to the catalyst solution prepared according to B, and there was a pronounced increase in the temperature of the batch, sometimes up to the boiling point. The amount of alkene and cumulene used, based on the number of double bonds, corresponded to the molar amount of H$_2$O$_2$ which was present. In the oxidation of alkynes, twice the amount of H$_2$O$_2$ was used per triple bond. After 5 to 30 minutes, the solution had again become colorless and the reaction had come to a stop, i.e. the equilibrium reached did not alter even after a relatively long time.

The excess H$_2$O$_2$ remaining in the solution was removed by dissolving the entire batch in 10 ml of tetrahydrofuran and adding 1 g of manganese dioxide MnO$_2$, i.e. an excess, to destroy the peroxide. After 10 min, the evolution of gas had ended. The suspension was filtered through a glass sinter filled with ®Celite (registered trade mark of Manville Corp., Denver, U.S.A.) and subsequently washed three times with tetrahydrofuran. The solvent was removed from the filtrate under reduced pressure. The crude product thus obtained was analytically pure after washing three times with 20 ml of n-hexane in each case. If necessary, the product was worked up by distillation or recrystallization, optionally at reduced temperature.

The use of an excess of H$_2$O$_2$ allows the yield to be significantly improved in many cases.

TABLE 1 for Oxidation reactions

| Example | Starting Material | Reaction conditions* | Products | Yield |
|---|---|---|---|---|
| 1 | Propylene | −10° C., 12 h | Propyleneoxide | 50%** |
|   |   |   | 1,2-Propanediol | 50% |
| 2 | 2-Butylene | −10° C., 10 h | 2,3-Butanediol | 100%** |
| 3 | 1-Pentene | RT, 1 h | 1,2-Epoxypentane | 55% |
| 4 | cis-2-Pentene | RT, 3 h | Pentane-2,3-diol | 10% |
|   |   |   | 2,3-Epoxypentane | 90% |
| 5 | 2-Methyl-1-butene | RT, 4 h | Epoxy-2-methyl-butane | 65% |
| 6 | 2,3-Dimethyl-2-butene | RT, 1 h | 2,3-Dimethyl-2,3-butanediol | 75% |
| 7 | 2-Methyl-1-hexane | RT, 3 h | 1,2-Epoxy-2-methylhexane | 55% |
| 8 | 1-Octene | RT, 3 h | 1,2-Octanediol | 70% |
| 9 | trans-4-Octene | RT, 2 h | 4,5-Epoxyoctane | 100% |
| 10 | 1-Decene | RT, 3 h | 1,2-Epoxydecane | 60% |
| 11 | Cyclohexene | RT, 1 h | Cyclohexane-1,2-diol(trans-Isomer) | 98% |
| 12 | 1-Methyl-1-cyclohexene | RT, 2 h | 1,2-Dihydroxy-1-methyl-cyclohexane | 70% |
| 13 | Cycloheptene | RT, 1 h | Epoxycycloheptane | 80% |
| 14 | Cyclooctene | RT, 1 h | Epoxycyclooctane | 80% |
| 15 | cis,cis-1,5- | RT, 2 h | 1,2,5,6-Diepoxy- | 80% |

TABLE 1-continued for Oxidation reactions

| Example | Starting Material | Reaction conditions* | Products | Yield |
|---|---|---|---|---|
| 16 | Cyclooctadiene Cycloooctate-traene | RT, 2 h | cycclooctane 1,2-Epoxy-3,5,7-cyclooctatriene | 35% |
| 17 | Cyclododecene | RT, 1 h | Epoxycyclododecane | 100% |
| 18 | 1,9-Cyclohexa-decadiene | RT, 3 h | 10-Epoxy-1-cyclo-hexadecene | 55% |
| 19 | α-Pinene | −30° C., 1 d | exo- and endo-Epoxypinane | 55% |
| 20 | Limonene | RT, 5 h | Limonene-mono-epoxide | 35% |
| 21 | Citral | RT, 1 d | 2,3-Epoxycitral | 28% |
| 22 | Squalene | RT, 2 h | Dihydroxysqualene | 75% |
| 23 | Allyl alcohol | RT, 10 h | 2,3-Epoxy-1-propanol | 90% |
| 24 | 2-Bromo-2-butene | RT, 2 h | 2,3-Epoxy-2-bromobutane | 45% |
| 25 | Diethyl maleate | RT, 1 d | Diethyl epoxy-succinate | 20% |
| 26 | Methyl oleate | RT, 1 d | methyl 9,10-Dihy-droxyoctadecanoate | 92% |
| 27 | Methyl linoleate | RT, 2 h | Methyl 6,7-Epoxy-linoleate | 80% |
| 28 | 1,4-Naphtho-quinone | 70° C., 18 h | 2,3-Epoxy-1,4-naphthoquinone | 64% |
| 29 | 3-Methyl-1,2-butadiene | RT, 1 h | 3-Hydroxy-3-methyl-2-butanone | 45% |
| 30 | 3-Hexyne | RT, 1 h | 4-Hexen-3-one | 40% |
| 31 | Diphenyl-acetylene | 65° C., 1 d | Benzil | 71% |
| 32 | Styrene | RT, 2 h | Phenylacetaldehyde (±)-Phenylethylene glycol Benzaldehyde | 12% 11% 25% |
| 33(a) | cis-Stilbene-(1,2-Diphenyl-ethylene) | 70° C., 2 h | Benzaldehyde cis-Stilbeneoxide | 76% 6% |
| (b) | cis-Stilbene-(1,2-Diphenyl-ethylene) | RT, 2 h | Benzaldehyde cis-Stilbeneoxide | 49 1% |
| 34 | 2,3,4,5,6-Pentafluoro-styrene | RT, 3 h | 2,3,4,5,6-Penta-fluorostyreneoxide | 56% |

*RT = Room temperature (about 28° C.). h = hour. d = day
**Yield based on converted olefin.

(35)

50 mg (0.2 mmol) of methylrhenium trioxide were dissolved with stirring at −10° C. in 135 ml of oxidation solution according to B. At this temperature, 25 ml of cyclohexene (20 g, 0.24 mol) were added dropwise over a period of 3 hours. Meanwhile, the color of the solution lightened somewhat. After the cyclohexene addition had been completed, the mixture was allowed to reach room temperature. Excess hydrogen peroxide was destroyed by stirring with 2 g of commercially available $MnO_2$ for a period of 1 hour. The suspension was filtered off through a D3 sinter/celite, subsequently washed three times with 20 ml of tetrahydrofuran in each case and the solvent was evaporated off in the vacuum of a rotary oil pump. The tacky residue was washed five times with 50 ml of n-hexane in each case and then dried under a high vacuum. Yield: 24.1 g of colorless, pulverulent 1,2-transcyclohexanediol (85%). Catalyst/product mole ratio, 1/1000.

(36) Oxidation using a compound containing 6-valent rhenium 20 mg of solid tetramethyltetraoxodirhenium (VI) $(CH_3)_4Re_2O_4$ were added to a 5 ml portion of the "oxidation solution" initially prepared according to B) from tertbutanol and $H_2O_2$. This immediately produced a yellow coloration. 0.15 ml of cyclododecene was then added. This caused slight heating of the solution. After 1 hour, the mixture was worked up as in Examples 1–34 and analyzed (GC/IR/MS). 99% pure epoxycyclododecane was obtained by this procedure.

Compounds of the formula III

Examples 37–52

(37) (1-Azabicyclo[2,2,2]octane)methyl(trioxo)rhenium (VII), $CH_3ReO_3 \cdot N(C_2H_4)_3CH$ To a solution of 70 mg (0.63 mmol) of quinuclidine $[N(C_2H_4)_3CH]$ in 10 ml of tetrahydrofuran were added at 20° C. with constant stirring 160 mg (0.64 mmol) of $CH_3ReO_3$. The initially colorless solution instantly turned lemon yellow when the quinuclidine was added. After one hour, the solvent was removed under reduced pressure. In this way, 210 mg (91%) of product were obtained in the form of small needle-like crystals. Recrystallization from tetrahydrofuran/n-pentane (ratio by volume 3:1) alows larger crystals to be grown. M.p. 112° C. (decomp.).

$C_8H_{16}NO_3Re$ calc.: C 26.65, H 4.44, N 3.89, (360.43) found: C 27.08, H 4.37, N 3.79.

$^{17}O$-NMR spectrum: $\delta O = 566$ ppm $[CH_2Cl_2/CDCl_3]$. The compound is characterized by single crystal X-ray structural analysis: d(Re-O) = 165-173 pm, d(Re-N) = 250 pm IR [KBr]: ν(Re≡O), cm$^{-1}$: 925 sst.

$^1$H-NMR [solvent] δ(ppm, 23° C.): 1.40 (s, 3H); 1.51 (dt, $^3$J(H,H) = 8.06 Hz, $^3$J(H,H) = 3.18 Hz, 6H); 1.81 (sept, $^3$J(H,H) = 3.18 Hz, 1H); 2.48 (T, $^3$J(H,H) = 8.06 Hz, 6H) [CDCl$_3$]

(38)
(1,4-Diazabicyclo[2,2,2]octane)-N,N'-bis[methyl(trioxo)rhenium(VII)], [CH$_3$ReO$_3$]$_2$. N(C$_2$H$_4$)$_3$N]

To a solution of 130 mg (0.52 mmol) of CH$_3$ReO$_3$ in 10 ml of tetrahydrofuran were added 58 mg (0.52 mmol) of 1,4-diazabicyclo[2,2,2]octane. This immediately caused the solution to turn deep yellow. After 1 hour, the solvent was removed under reduced pressure and the yellow, finely crystalline product was recrystallized at −30° C. from tetrahydrofuran. The yield of analytically pure product was 160 mg (85%).

C$_8$H$_{16}$N$_2$O$_6$Re$_2$ calc.: C 15.73, H 2.95, N 4.59, O 15.72; (610.65) found: C 15.78, H 2.95, N 4.47, O 15.74.

IR [KBr]: ν(Re≡O), cm$^{-1}$: 909 sst $^1$H-NMR [solvent] δ(ppm, 23° C.): 1.47 (s, 6H); 2.55 (s, 12H) [CDCl$_3$]

(39) (Aniline)methyl(trioxo)rhenium(VII), CH$_3$ReO$_3$.NH$_2$C$_6$H$_5$

36 μl (37 mg, 0.40 mmol) of freshly distilled aniline were added to a solution of 100 mg (0.40 mmol) of CH$_3$ReO$_3$ in 10 ml of toluene. This caused the color to change immediately to yellow. After 15 min, the solvent was removed under reduced pressure and the residue was sublimed at 40° C. (1.33×10$^{-3}$ mbar). In this way 120 mg (88%) of product were obtained as bright yellow crystals.

C$_7$H$_{10}$NO$_3$Re calc.: C 24.56, H 2.94, N 4.09, O 14.02, Re 54.39; (342.37) found: C 24.49, H 2.99, N 4.09, O 13.81, Re 54.62.

$^{17}$O-NMR spectrum: δO = 566 ppm [CH$_2$Cl$_2$/CDCl$_3$].

The compound is further characterized by single crystal X-ray structural analysis: d(Re-O) = 169.9 pm; d(Re-N) = 246.9 pm; NH$_2$ . . . O hydrogen bonds are present.

IR [KBr]: ν(Re≡O), cm$^{-1}$: 927 sst.

$^1$H-NMR [solvent] δ(ppm, 23° C.): 2.57 (s, 3H); 3.62 (br, 2H); 6.67 (dd, $^3$J(H,H) = 7.32 Hz, $^4$J(H,H) = 1.22 Hz, 2H); 6.75 (t, $^3$J(H,H) = 7.32 Hz, 1H); 7.14 (m; 2H) [CDCl$_3$]

(40) (2,2'-Bipyridine)methyl(trioxo)rhenium(VII), CH$_3$ReO$_3$.C$_{10}$H$_8$N$_2$ A slight excess (0.79 g, 4.4 mmol) of 2,2'-bipyridine is added at room temperature with constant vigorous stirring to a solution of 1.00 g (4.0 mmol) of CH$_3$ReO$_3$ in 100 ml of toluene. A yellow precipitate was immediately formed. After a reaction time of 30 min, the precipitate was allowed to settle and the solvent was decanted off. Excess 2,2'-bipyridine was removed by washing three times with 25 ml of toluene in each case. This procedure was repeated twice using n-pentane. The solvent was finally removed under an oil pump vacuum. In this way 1.59 g (97%) of the compound were obtained analytically pure.

M.p. 138° C. (decomp.).

C$_{11}$H$_{11}$N$_2$O$_3$Re calc.: C 32.56, H 2.71, N 6.91, O 11.84; (405.43) found: C 32.68, H 2.74, N 6.80, O 12.02.

IR [KBr]: ν(Re≡O), cm$^{-1}$: 910 sst, 940 sst $^1$H-NMR [solvent] δ(ppm, 23° C.): 1.95 (s, 3H); 7.35 (m, 2H); 7.87 (m, 2H); 8.50 (d, $^3$J(H,H) = 7.93 Hz, 2H); 8.66 (d, $^3$J(H,H) = 4.88 Hz, 2H) [CD$_2$Cl$_2$]

(41) (2,2'-bipyridine)methyl(oxo)dichlororhenium(V), CH$_3$ReOCl$_2$.C$_{10}$H$_8$N$_2$ To 0.50 g (1.23 mmol) of a suspension of the compound according to Example 30 in 30 ml of methylene chloride were added dropwise at room temperature with constant stirring 314 μl (2.44 mmol) of freshly distilled trimethylchlorosilane. Then an equimolar amount (322 mg; 1.23 mmol) of triphenylphosphane was added. The solution immediately turned deep violet in color. Then the reaction mixture was boiled under reflux until the violet color had completely disappeared and the reaction solution had become yellowish brown (reaction time about 1 hour). After cooling the solution to room temperature, the product was quantitatively precipitated by adding 60 ml of n-pentane and the solvent, which was now only faintly red in color, was decanted off. The product was purified by washing several times with 10 ml of toluene in each case. Recrystallization from methylene chloride at −30° C. allowed small, cubic crystals to be grown. The compound was obtained in 98% yield (0.54 g).

C$_{11}$Cl$_2$H$_{11}$N$_2$ORe (444.33): calc.: C 29.73, H 2.50, N 6.30, O 3.60, Cl 15.96; found: C 29.64, H 2.51, N 6.20, O 3.63, Cl 16.01.

IR [KBr]: ν(Re≡O), cm$^{-1}$: 988 sst $^1$H-NMR [solvent] δ(ppm, 23° C.): 5.41 (s,3H); 7.09 (m, 1H); 7.46 (m, 1H); 7.63 (m, 1H); 7.90 (m, 1H); 8.00 (m, 2H); 8 36 (m, 1H); 8.47 (m, 1H) [CD$_2$Cl$_2$]

(42)
(2,2'-Bipyridine)methyl(oxo)bis(trimethylsilylmethyl)-rhenium(V), CH$_3$ReO[CH$_2$Si(CH$_3$)$_3$]$_2$.C$_{10}$H$_8$N$_2$ A solution of 1.0 ml of (trimethylsilyl)methylmagnesium chloride, (CH$_3$)$_3$SiCH$_2$MgCl (1.0 molar solution in diethyl ether; 1.0 mmol), was diluted with 10 ml of toluene and then cooled to −78° C. and finally to this solution a suspension, likewise at −78° C., of 175 mg (0.39 mmol) of the compound according to Example 41 in 20 ml of toluene was added. The reaction mixture was then brought to room temperature in the course of 2 hours. Above about −30° C., a slight greenish coloration was observed; finally, a bluish green solution was obtained. After the solution had reached room temperature, it was stirred for 1 hour and finally the solvent was removed under an oil pump vacuum. The residue was introduced into a chromatography column and subjected to chromatography at 10° C. on silica gel (supplied by Merck; kieselgel 60, particle size 0.063–0.200 mm). The product was eluted as the deep-green zone with n-pentane/toluene (ratio by volume 1:1). This solvent mixture is suitable for growing single crystals. The eluate was subjected to evaporation in an oil pump vacuum to obtain 60 mg (28%) of compound which was insensitive to air and water.

C$_{19}$H$_{33}$N$_2$OReSi$_2$ calc.: C 41.65, H 6.07, N 5.11; (547.86) found: C 41.72, H 6.36, N 4.42.

IR (KBr): ν(Re≡O), cm$^{-1}$: 975 sst $^1$H-NMR [solvent] δ(ppm, 23° C.): 0.34 (s, 18H); 2.22 (d, $^2$J(H,H) = 10.98 Hz , 2H); 3.15 (d, $^2$J(H,H) = 10.98 Hz, 2H); 3.67 (s, 3H); 5.89, 6.26, 6.35, 6.58, 6.69, 7.19, 7.71, 8.72 (m, 8H) [d$^8$-toluene]

(43) (2,2'-Bipyridine)trimethyl(oxo)rhenium, $(CH_3)_3ReO \cdot C_{10}H_8N_2$ To a suspension of 888 mg (2.0 mmol) of the compound according to Example 41 in 60 ml of toluene were added dropwise at $-78°$ C. with constant stirring 2.69 ml of methyllithium (1.6 molar solution in diethyl ether; 4.3 mmol). The reaction solution was stirred at this temperature for about 30 min and then brought to room temperature over a period of 3 hours. A reaction was already brought about at a temperature of $-65°$ C. (green coloration of the reaction mixture). After 3 hours, the deep green colored solution had reached room temperature and depositing of a fine precipitate of LiCl was observed. The solvent was then removed under reduced pressure and the dark, almost black residue was extracted by being taken up in toluene. The deep green solution was filtered through ®Celite to remove completely the precipitated LiCl and the solvent was then evaporated off under reduced pressure. 726 mg (90%) of compound were obtained as an almost black powder which was stable in air and which dissolved in n-pentane and toluene giving a deep green color, in diethyl ether, tetrahydrofuran and acetone giving a deep blue color, and in methylene chloride and chloroform giving a turquoise color.

$C_{13}H_{17}N_2ORe$ calc.: C 38.67, H 4.24, N 6.94, O 3.97. (403.40) found: C 38.70, H 4.10, N 6.79, O 4.00.

IR [KBr]: $v(Re=O)$, $cm^{-1}$: 976 sst $^1$H-NMR [solvent] $\delta$(ppm, 23° C.): 2.40 (s,6H); 3.47 (s, 3H); 6.84, 7.19, 7.57, 7.86, 7.91, 8.28, 8.79, (m, 8H) [CDCl$_3$]

(44–46) Isomers of(methoxyaniline)methyl(trioxo)rhenium(VII), $CH_3ReO_3 \cdot CH_3OC_8H_4NH_2$ To a solution of 80 mg (0.32 mmol) of $CH_3ReO_3$ in 10 ml of toluene were added 40 mg (0.33 mmol) of the corresponding substituted aniline derivative, the solution immediately turning yellow. After 30 min. the volume of solvent was reduced to half using an oil pump vacuum. Then 10 ml of n-hexane were added. In each case, the produce (Examples 44–46) crystallized out at $-35°$ C. and was then dried over a high vacuum.

(44) 2-Methoxyaniline compound: yellow crystals; yield 110 mg (92%)

$C_8H_{12}NO_4Re$ calc.: C 25.80, H 3.25, N 3.76; (372.40) found: C 25.75, H 3.15, N 3.76.

IR [KBr]: $v(Re=O)$, $cm^{-1}$: 929 sst $^1$H-NMR [solvent] $\delta$(ppm, 23° C.): 2.58 (s, 3H); 2.90 (br, 2H); 3.83 (s, 3H); 6.77 (m, 4H) [CDCl$_3$]

(45) 3-Methoxyaniline compound: yellowish brown crystals; yield 110 mg (92%).

$C_8H_{12}NO_4Re$ calc.: C 25.80, H 3.25, N 3.76; (372.40) found: C 25.73, H 3.23, N 3.77.

IR [KBr]: $v(Re=O)$, $cm^{-1}$: 915 sst, 944 st, 962 st $^1$H-NMR [solvent] $\delta$(ppm, 23° C.): 2.59 (s, 3H); 3.75 (s, br, 5H); 6.23 (t, $^4J(H,H)=2.44$ Hz, 1H); 6.27 (dt, $^3J(H,H)=7.93$ Hz, $^4J(H,H)=1.22$ Hz, 1H); 6.31 (dd, $^3J(H,H)=9.16$ Hz, $^4J(H,H)=2.44$ Hz, 1H); 7.04(t, $^3J(H,H)=7.93$ Hz) [CDCl$_3$]

(46) 4-Methoxyaniline compound: reddish brown crystals; yield 110 mg (92%).

$C_8H_{12}NO_4Re$ calc.: C 25.80, H 3.25, N 3.76. (372.40) found: C 25.93, H 3.12, N 3.72.

IR [KBr]: $v(Re=O)$, $cm^{-1}$: 909 sst, 934 sst, 962 st $^1$H-NMR [solvent] $\delta$(ppm, 23° C.): 2.56 (s, 3H); 3.39 (br, 2H); 3.73 (s, 3H); 6.63 (d, $^3J(H,H)=9.16$ Hz, 2H); 6.73 (d, $^3J(H,H)=8.13$ Hz, 2H) [CDCl$_3$]

(47) [2-(Aminomethyl)pyridine]methyl(trioxo)rhenium(-VII), $CH_3ReO_3 \cdot NC_5H_4CH_2NH_2$ 33 μl (35 mg, 0.32 mmol) of 2-(aminomethyl)pyridine were added to a solution of 80 mg (0.32 mmol) of $CH_3ReO_3$ in 10 ml of toluene. A yellow precipitate was immediately formed from which the supernatant was decanted, and then the solid was washed twice with 10 ml of toluene in each case and finally dried under an oil pump vacuum. In this way 110 mg (quantitatively) of yellow product were obtained.

$C_7H_{11}N_2O_3Re$ calc.: C 23.53, H 3.10, N 7.84, O 13.43, Re 52.10; (357.38) found: C 23.73, H 3.08, N 7.78, O 13.70, Re 52.05.

IR [KBr]: $v(Re=O)$ $cm^{-1}$: 908 sst, 935 sst $^1$H-NMR [solvent] $\delta$(ppm, 23° C: 2.12 (s, 3H); 3.53 (br, 2H); 5.04 (d, $^2J(H,H)=22.0$ Hz, 1H); 6.09 (d, $^2J(H,H)=22.0$ Hz, 1H); 8.19 (m, 1H); 8.30 (m, 1H); 8.83 (m, 1H); 9.23 (m, 1H) [CD$_3$CN]

(48) [N-(2-Aminoethyl)pyrrolidine]methyl(trioxo)rhenium(-VII), $CH_3ReO_3 \cdot (C_4H_8N-CH_2CH_2NH_2)$ 41 μl (37 mg, 0.32 mmol) of N-(2-aminoethyl)pyrrolidine were added to a solution of 80 mg of $CH_3ReO_3$ (0.32 mmol) in 10 ml of toluene. A yellow coloration was immediately produced. After about 30 sec., a yellow precipitate formed. The supernatant was decanted off; the solid was then washed with 10 ml of toluene and the solvent removed under an oil pump vacuum. 100 mg (85%) of compound were obtained as a yellow powder.

$C_7H_{17}N_2O_3Re$ calc. C 23.13, H 4.72, N 7.71. (363.43) found: C 23.31, H 4.64, N 7.61.

(9) [(N,N-dimethylamino)acetonitrile]methyl(trioxo)rhenium(VII), $CH_3ReO_3 \cdot [(CH_3)_2NCH_2CN]$ 24 mg (27 μl, 0.28 mmol) of (N,N-dimethylamino)acetonitrile were added to a solution of 70 mg (0.28 mmol) of $CH_3ReO_3$ in a mixture of 5 ml of toluene and 5 ml of n-pentane. When the light yellow colored solution was cooled to $-35°$ C., 80 mg (86%) of yellowish translucent crystals were formed in the course of 20–30 h and these were dried under an oil pump vacuum.

$C_5H_{11}N_2O_3Re$ calc.: C 18.02, H 3.33, N 8.40; (333.36) found: C 17.91, H 3.28, N 8.04.

(50) [(N,N-Dimethylamino)acetone]methyl(trioxo)rhenium(VII), $CH_3ReO_3 \cdot [(CH_3)_2NCH_2C(O)CH_2]$ To a solution of 70 mg (0.28 mmol) of $CH_3ReO_3$ in 10 ml of n-pentane were added 28 mg (32 μl, 0.28 mmol) of (N,N-dimethylamino)acetone. The initially colorless solution immediately turned yellow. The solution was then left to crystallize at $-35°$ C. for 10–30 h. 80 mg (82%) of compound were obtained in the form of yellow platelets.

$C_8H_{14}NO_4Re$ calc.: C 20.57, H 4.03, N 4.00; (350.39) found: C 20.84, H 4.02, N 3.99.

(51) Methyl(pyridine-N-oxide)trioxorhenium(VII), $CH_3ReO_3 \cdot ONC_5H_5$ 70 mg (0.28 mmol) of $CH_3ReO_3$ and 60 mg (0.64 mmol) of pyridine-N-oxide were mixed in 10 ml of toluene. A colorless solution was formed. This was kept at $-35°$ C. After 10 to 30 hours, the compound crystallized in the form of yellow needles. The product was dried under a high vacuum.

Yield: 80 mg (80%).

$C_6H_8NO_4Re$ calc.: C 20.93, H 2.34, N 4.07; (344.34) found: C 21.12, H 2.45, N 4.07.

(52) Methyl[tricarbonyl($\eta^5$-pyrrolyl)manganese]trioxorhenium(VII), $CH_3ReO_3 \cdot [(\eta^5-C_4H_4N)]Mn(CO)_3$ To a solution of 70 mg (0.34 mmol) of tricarbonyl($\eta^5$-pyrrolyl)manganese, $(\eta^5-C_4H_4N)Mn(CO)_3$, in 10 ml of diethyl ether, were added 85 mg (0.34 mmol) of $CH_3ReO_3$. After 20 hours' stirring at room temperature, the mixture was filtered. 10 ml of n-hexane was added to the filtrate and the solution was allowed to crystallize at $-35°$ C. for 10-30 hours. Yield: 110 mg (71%); yellowish brown crystals.

$C_6H_7MnNO_8Re$ calc.: C 21.15, H 1.55, Mn 12.00, N 3.08; (454.29) found: C 21.27, H 1.59, Mn 12.09, N 3.10.

Examples 53–56

Oxidation using compounds III

To 2.68 ml of the oxidation solution initially obtained according to B were added 20 mg of $CH_3ReO_3 \cdot L$. Meanwhile, an immediate yellow coloration was observed. To the catalyst solution prepared in this way was added 0.5 ml of cyclohexene. In the course of 3 h the yellow coloration disappeared and the reactant/product ratio which had been reached remained constant. The mixture was subsequently worked up as indicated in Examples 1 to 34. The results can be seen in Table 2 below.

TABLE 2

| Example | Ligand L | Reaction conditions | Products | Yield |
|---|---|---|---|---|
| 53 | m-Anisidine | RT, 20 h | 1,2-cyclohexanediol | 50% |
| 54 | p-Anisidine | RT, 20 h | 1,2-cyclohexanediol | 55% |
| 55 | Methylephedrine | RT, 20 h | Epoxycyclohexane | 75% |
| 56 | Dimethylaminoacetonitrile | RT, 20 h | 1,2-cyclohexanediol | 51% |

*RT = room temperature (about 28° C.)

Examples 57–63

Oxidation catalyst fixed on a polymer

To a suspension of 9.20 g of poly(4-vinylpyridine) (commercial product "Reilllex" supplied by Aldrich Chemie GmbH, Steinheim/Albuch, catalog No. 22,696-3) in 200 ml of tetrahydrofuran was added 0.80 g (3.2 mmol) of $CH_3ReO_3$ and the mixture was thoroughly stirred for 20 hours using a magnetic stirrer. During this period, the polymer changed from colorless to bright yellow with the formation of a complex of $CH_3ReO_3$. The solvent was then decanted off. The residue was washed five times with 20 ml of tetrahydrofuran each time and finally dried under an oil pump vacuum. A yellow powder remained. The results of the elemental analysis (Re calculated 6.0, found 6.1%) showed that the $CH_3ReO_3$ had become bound to the polymer substrate without losses. This measure greatly reduced the volatility of $CH_3ReO_3$: the compound could no longer be removed from the substrate at temperatures up to 150° C. even under a high vacuum.

Similar catalysts in which $CH_3ReO_3$ had been taken up on polymers were obtained by the same procedure using

| | | |
|---|---|---|
| 58) | Poly(2-vinylpyridine) | (Aldrich No. 18,950-2) |
| 59) | Poly(2-vinylpyridine-co-styrene) | (Aldrich No. 18,127-7) |
| 60) | Poly(acrylamide) | (Aldrich No. 19,207-4) |
| 61) | Poly(vinylpyrrolidone) | (Aldrich No. 85,648-7) |
| 62) | Polyimide | (Aldrich No. 18,464-0) |
| 63) | Nylon 6 | (Aldrich No. 18,111-0) |

Examples 64–66

Oxidation using methylrhenium trioxide fixed to a polymer

To 3 ml of the oxidation solution initially obtained according to B were added 20 mg of the catalyst according to Example 57. The insoluble, catalyst-containing polymer immediately turned yellow in color. To the suspension was added with stirring the olefin to be oxidized, during which heating was observed. After 1 hour, the yellow coloration of the polymer had disappeared and the reactant/product ratio which had been reached remained constant even after a relatively long waiting period. After a further 30 min, the catalyst was filtered off on a glass sinter and washed three times with 20 ml of tetrahydrofuran each time. After drying under an oil pump vacuum, the catalyst can be used for further oxidation batches. The filtrate was worked up as described in Examples 1–34. The results are summarized in Table 3.

TABLE 3

| Example | olefin | Reaction conditions* | Products | Yield |
|---|---|---|---|---|
| 64 | Cyclohexene | RT, 20 h | epoxycyclohexane | 27% |
| 65 | Methyl oleate | RT, 20 h | methyl 9,10-epoxyoctadecanoate | 85% |
| 66 | Allyl alcohol | RT, 20 h | 1,2-epoxypropane-3-ol | 20% |

*RT = room temperature (about 28° C.)

We claim:

1. A compound of the general formula $$(R^{11}Re)_kO_lR^{12}{}_m \cdot L_n \qquad (III),$$

wherein
$R^{11}$ is a non-aromatic hydrocarbon group of 1 to 10 carbon atoms or aralkyl of 7 to 9 carbon atoms, each being bound to rhenium by a carbon atom bearing at least one hydrogen atom,
$R^{12}$ is an aliphatic hydrocarbon group having 1 to 10 carbon atoms which may contain up to 3 silicium bridging atoms, or is a phenyl group which is unsubstituted or contains up to 3 substituents selected from the group consisting of alkyl, alkoxy and combinations thereof, said substituents containing at most 6 carbon atoms or containing up to 5 fluorine atoms, L is a ligand which is bound to the rhenium via 1 to 3 atoms of at least one element selected from the group consisting of oxygen and nitrogen, and in which indices k is 1 or 2, l is an integer from 1 to 3·k, m is zero or an integer from 1 to 2·k and n is an integer from 1 to 3 k and the indices k, l, m and n are selected such that their combination conforms to the 5- to 7-valency of rhenium.

2. A compound of the formula $$(\text{polymer})_f (CH_3ReO_3)_g \qquad (VI)$$

in which the $CH_3ReO_3$ $3ReO3$ is bound to the polymer via amino nitrogen or amido nitrogen of the polymer and in which the quotient g/f represents the ratio by weight of the two components and is in the range of from 0.01 to 0.2.

3. A compound as claimed in claim 2, wherein the quotient g/f is in the range of from 0.02 to 0.1.

4. A catalyst for the oxidant of C—C-multiple bonds comprising at least one compound selected from the group consisting of a) a compound of the formula $$(R^{11}Re)_k O_l R^{12}{}_m \cdot L_n \qquad (III),$$

wherein

R$^{11}$ is a non-aromatic hydrocarbon group of 1 to 10 carbon atoms or aralkyl of 7 to 9 carbon atoms, each being bound to rhenium by a carbon atom bearing at least one hydrogen atom, R$^{12}$ is an aliphatic hydrocarbon group having 1 to 10 carbon atoms which may contain up to 3 silicium bridging atoms, or is a phenyl group which is unsubstituted or contains up to 3 substituents selected from the group consisting of alkyl, alkoxy and combinations thereof, said substituents containing at most 6 carbon atoms or containing up to 5 fluorine atoms, L is a ligand which is bound to the rhenium via 1 to 3 atoms of at least one element selected from the group consisting of oxygen and nitrogen, and in which the indices k is 1 or 2, l is an integer from 1 to 3·k, m is zero or an integer form 1 to 2·k and n is an integer from 1 to 3·k and the indices k, l, m and n are selected such that their combination conforms to the 5- to 7-valency of rhenium, and b) a compound of the formula $$(\text{polymer})_f (CH_3ReO_3)_g \qquad (VI)$$

in which the $CH_3ReO_3$ is bound to the polymer via amino nitrogen or amido nitrogen of the polymer and in which the quotient g/f represents the ratio by weight of the two components and is in the range of from 0.01 to 0.2.

5. A compound as claimed in claim 1, wherein the general formula (III)

R$^{11}$ is an alkyl radical having 1 to 10 carbon atoms or an cycloalkyl radical having 5 to 10 carbon atoms, R$^{12}$ is a linear or branched aliphatic hydrocarbon radical having 1 to 10 carbon atoms, and L is a member of the group consisting of an amine, an aliphatic azacycle, an aromatic azacycle, a O,O'-, N,O- and N,N'-chelate ligand, a substituted piperazine, an aminosubstituted piperidine, an aminosubstituted pyrrolidine, a methoxysubstituted pryidine, a 1,3-diketone, a 1,2-diketone, a β-aminoalcohol, a β-aminoaldehyde, a β-aminoketone, a 1,2-diimide, a β-aminoether, an aromatic N-oxide, a 1,2-diamine and a hydroxycarboxylic acid.

6. A compound as claimed in claim 1, wherein R$^{11}$ is methyl, the index k is 1, the index l is 3 and the index m is zero.

7. A compound as claimed in claim 2, wherein the polymer is poly(4-vinylpyridine), poly(2-vinylpyridine), poly(2-vinylpyridine-co-styrene), poly(acrylamide), poly(vinylpyrrolidone), polyimide or nylon 6.

8. A compound as claimed in claim 1 which is a member of the group consisting of $CH_3ReO_3.N(C_2H_4)_3CH$, $(CH_3ReO_3).(N(C_2H_4)_3N)$, $CH_3ReO_3.NH_2C_6H_5$, $CH_3ReO_3.C_{10}H_8N_2$, $CH_3ReOCl_2.C_{10}H_8N_2$, $CH_3ReO(CH_2Si(CH_3)_3)_2.C_{10}H_8N_2$, $(CH_3)_3ReO.C_{10}H_8N_2$, $CH_3ReO_3.CH_3OC_6H_4NH_2$, $CH_3ReO_3.NC_5H_4CH_2NH_2$, $CH_3ReO_3(C_4H_8N.CH_2CH_2NH_2)$, $CH_3ReO_3.((CH_3)_2NCH_2CN)$, $CH_3ReO_3.((CH_3)_2NCH_2C(O)CH_3)$, $CH_3ReO_3.ONC_5H_5$ and $CH_3ReO_3. ((n^5-C_4H_4N))Mn(CO^-)_3$.

* * * * *

UNITED STATES PATENT AND TRADEMARK OFFICE
CERTIFICATE OF CORRECTION

PATENT NO. : 5,155,247
DATED : October 13, 1992
INVENTOR(S) : Herrmann, et al.

It is certified that error appears in the above-identified patent and that said Letters Patent is hereby corrected as shown below:

In column 19, line 16, please correct the formula to read --$CH_3ReO_3$--.

In column 19, line 24, please correction "oxidant" to read --oxidation--.

In column 20, line 13, please insert the word --in-- after the word "wherein".

In column 20, line 40, please correct the formula to read

--$CH_3ReO(CH_2Si(CH_3)_3)_2 \cdot C_{10}H_8N_2$--.

In column 20, line 42, please correct the formula to read

--$CH_3ReO_3 \cdot NC_5H_4CH_2NH_2$--.

Signed and Sealed this

Second Day of November, 1993

Attest:

BRUCE LEHMAN

Attesting Officer

Commissioner of Patents and Trademarks